United States Patent [19]

Batson

[11] Patent Number: Plant 6,292

[45] Date of Patent: Sep. 13, 1988

[54] *DIEFFENBACHIA MACULATA* NAMED REBECCA'S JEWEL

[75] Inventor: Gene A. Batson, Zellwood, Fla.

[73] Assignee: Casa Flora, Inc., Dallas, Tex.

[21] Appl. No.: 906,220

[22] Filed: Sep. 11, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A new variety and distinct variety of *Dieffenbachia maculata* named Rebecca's Jewel having the characteristics of bright yellow-green to near white foliage with green edges and blotches, clumping habit, vigorous, full and compact growth habit, short nodes, thicker caliper stems, and its ease of propagation.

2 Drawing Sheets

The present invention comprises a new and distinct cultivar of *Dieffenbachia maculata,* known by the cultivar name Rebecca's Jewel.

The new cultivar was discovered growing among a group of plants of the parent cultivar in the greenhouses of Batson's Greenhouse, 5555 Round Lake Road, Box 641, Zellwood, Fla. 32798, in winter 1983. The parent plant was *Dieffenbachia maculata* cv. Camille, which had been used for propagation purposes for pot plant production. The source of supply of the parent plant of Camille was Pan American Seed Company, Paris, Fla. Single liners received from such source were propagated by tissue culture. The new cultivar is a mutation of the parent Camille, and was immediately recognized, after growing 4–5 weeks, for its distinctively different characteristics when compared with the other plants of the parent cultivar, with the compact habit and uniqueness of the leaf color of the new cultivar being particularly apparent.

After separating the new cultivar from the plants of the propagation bed of the parent cultivar, the new cultivar was asexually reproduced at Batson's Greenhouse, Zellwood, Fla., by the present inventor by taking vegetative cuttings and separating it into divisions from the new cultivar. Horticultural examination of subsequent generations of propagation has clearly demonstrated that the combination of characteristics as herein disclosed for Rebecca's Jewel are firmly fixed, and are retained through successive generations of asexual reproduction, with no changes in plant characteristics.

Rebecca's Jewel has not been observed under all possible environmental conditions. The phenotype may vary significantly with variations in environment such as temperature, light intensity, and day length. The observations, measurements, and comparisons describe plants grown in Zellwood, Fla., and Dallas, Tex., under greenhouse conditions which approximate those generally used in commercial practice.

The following traits have been repeatedly observed, and are determined to be basic characteristics of Rebecca's Jewel which, in combination, distinguish it as a new and distinct cultivar:

1. Excellent vigor.

2. Compact growth habit thereby permitting the plant to be readily grown for production in cell packs.

3. Perhaps its most distinctive habit is its bright yellow/white leaves with small blotches of green scattered through the bright area of the leaves and with a relatively small margin of green around the edge of the leaves.

4. It is dwarf, clumping and basal branching at nodes, as opposed to other Dieffenbachia plants, including its parent.

5. Due to the shorter leaf petioles, the clumping characteristic, and hanging leaves, it gives a more full, rounded effect than the parent cultivar.

6. Due to the bushy branching characteristics and ease of rooting of tip-cuttings, the plant can be easily propagated.

7. Stem caliper is greater, giving the plant a stronger stem.

8. Rebecca's Jewel has not produced a flower, thereby requiring reproduction through asexual techniques.

9. Due to its smaller and compact growth habit, it is suitable for dish gardens, 4" and 6" pot production.

10. The attractive yellow/white and green leaves can be consistently maintained by a feeding solution including nutrients so as to prevent a yellowing of the green portion of the leaf.

11. Disease resistance of Rebecca's Jewel has been excellent. To date, no plant disease has appeared.

12. All of the above characteristics together result in an outstanding new cultivar, and market research to date has indicated a probable wide acceptance of the new cultivar.

In the accompanying photographic drawings,

Sheet 1 is a perspective view of the new cultivar grown in a 6" pot.

Sheet 2 is a comparison color photograph showing the new cultivar in the middle, the parent cultivar Camille on the left, and Compacta on the right. Compacta is the parent cultivar of Camille.

Attached is Chart A, which compares certain characteristics of Rebecca's Jewel with the same characteristics of Compacta and the parent cultivar Camille. The measurements appearing in the chart were based on observations and measurements of the cultivars grown simultaneously in the greenhouses of Casa Flora, Inc., Dallas, Tex. The chart was prepared by Southern Methodist University Herbarium. The compactness of Rebecca's Jewel will be particularly apparent from the comparative measurements. Generally, the habit, shape, and form of Rebecca's Jewel is very similar to Compacta and Camille. Rebecca's Jewel tends to be a little more compact, due to mostly the shorter petioles, thus keeping the blades more bunched together.

In the following description, color references are made to The Royal Horticultural Society Colour Chart (R.H.S.). The color values were determined at approximately 10:00 a.m. in early September of 1986, under natural light in Alexandria, Va.

THE PLANT

Botanical: *Dieffenbachia maculata* cv. Rebecca's Jewel.
Origin: Mutation of *Dieffenbachia maculata* cv. Camille.
Form: Short, compact, clustered stems with abundant foliage; mostly leafy in the upper parts of the stems.
Shape: Compact with an irregular top growth; leaves firm and coming off the stem at 45 degree angles, not drooping.
Growth: Excellent vigor.
Stem: Stem size varies with larger ones 10–12 cm in diameter, sometimes horizontal at base.
Root: Easily rooted.
Internodes: Internodes vary from 10–12 mm long.
Foliage:

*Quantity.*—Leaf blades numerous and compact. The relatively short internodes and petioles help to create a lush foliage aspect.

*Texture.*—Canaliculate (somewhat channeled) with raised midrib and recessed lateral veins.

*Color.*—Predominant upper surface color is yellow-green 145D infused with varying amounts of 145C and 145B, with the predominant color in certain instances turning to a near white 157A-B. The variegation pattern makes it very difficult to state precise color values, but all of the values noted above appear on specimen leaves and in the photographic drawings. The edge is banded with a generally green 137B-C, with blotches of the same color appearing irregularly in the interior away from the edge. The same colors appear in the undersurface, which is somewhat shiny.

*Shape.*—Blades oblong-elliptic to oblong-lanceolate, 7–8 cm broad and 15–16 cm long, lobeless and toothless, rounded at base, apex acuminate-cuspidate.

*Petioles.*—Averaging 9 cm long, leaf sheaths averaging 6.5 cm long.

*Flowers.*—Unknown.

Disease resistance: Good as compared with parent cultivar grown under the same conditions in Zellwood, Fla., and Dallas, Tex. No diseases have been detected to date during propagations through ten generations.
Other characteristics:

*Nutrient feeding.*—The intense bright leaf with yellow-green to near white mid-leaf color can be maintained during low light periods by the application of 200 ppm of Peters Soluble Fertilizer (20-20-20). In periods of longer day length, Peters Fertilizer (20-20-20) can be applied in amounts up to 300 ppm.

*Clumping habit.*—Another distinctive characteristic is the dwarfish clumping and basal branching habit with relatively few runners.

CHART A

Comparison of Rebecca's Jewel, Compacta, and Camille

Foliage:

*Quantity.*—Rebecca's Jewel — Leaves numerous and compact because of shorter petioles. Camille — Numerous leaves, but less compact. Compacta — Numerous leaves, but less compact.

*Color.*—Rebecca's Jewel — Upper surface prominently dull yellow-green to white with dull green blotches and irregular marks. Lower surface somewhat shiny. An average of 65–75% of the leaf blade is blotched or yellow-green to near white in color. Compacta — Upper surface prominently dull green with yellow/green to white blotches and irregular marks. Lower surface somewhat shiny. An average of only 30–50% of the leaf blade is blotched or yellow/-green-white in color. Camille — Upper surface dull with central part of blade paralleling mid-rib yellow/green to white and no blotches or irregular marks. Lower surface somewhat shiny. An average of 50–60% of the leaf blade is solid with the yellow/green-white color and unblotched or marked.

*Shape.*—Rebecca's Jewel — Larger leaf blades oblong-elliptic to oblong-lanceolate, 7–8 cm broad, and 15–16 cm long, lobeless and toothless, rounded at base, apex acuminate-cuspidate. Compacta — Larger leaf blades ovate to oblong-elliptic to oblong-lanceolate 8–9 cm broad, and 16–17 cm long, lobeless and toothless, rounded at base, apex acuminate to occasionally cuspidate. Camille — Larger leaf blades about the same as Rebecca's Jewel, except 17–18 cm long, and apex which is like Compacta.

*Petioles.*—Rebecca's Jewel — Averaging 9 cm long, leaf sheath averaging 6.5 cm long. Camille — Averaging 105 cm long, leaf sheath averaging 6.5 cm long.

*Flowers.*—Rebecca's Jewel — Unknown. Compacta — Unknown. Camille — Unknown.

I claim:

1. A new and distinct variety of *Dieffenbachia maculata* named Rebecca's Jewel, as illustrated and described, and particularly characterized by its bright yellow-green to near white foliage with green edges and blotches, clumping habit, vigorous, full and compact growth habit, short nodes, thicker caliper stems, and its ease of propagation.

* * * * *

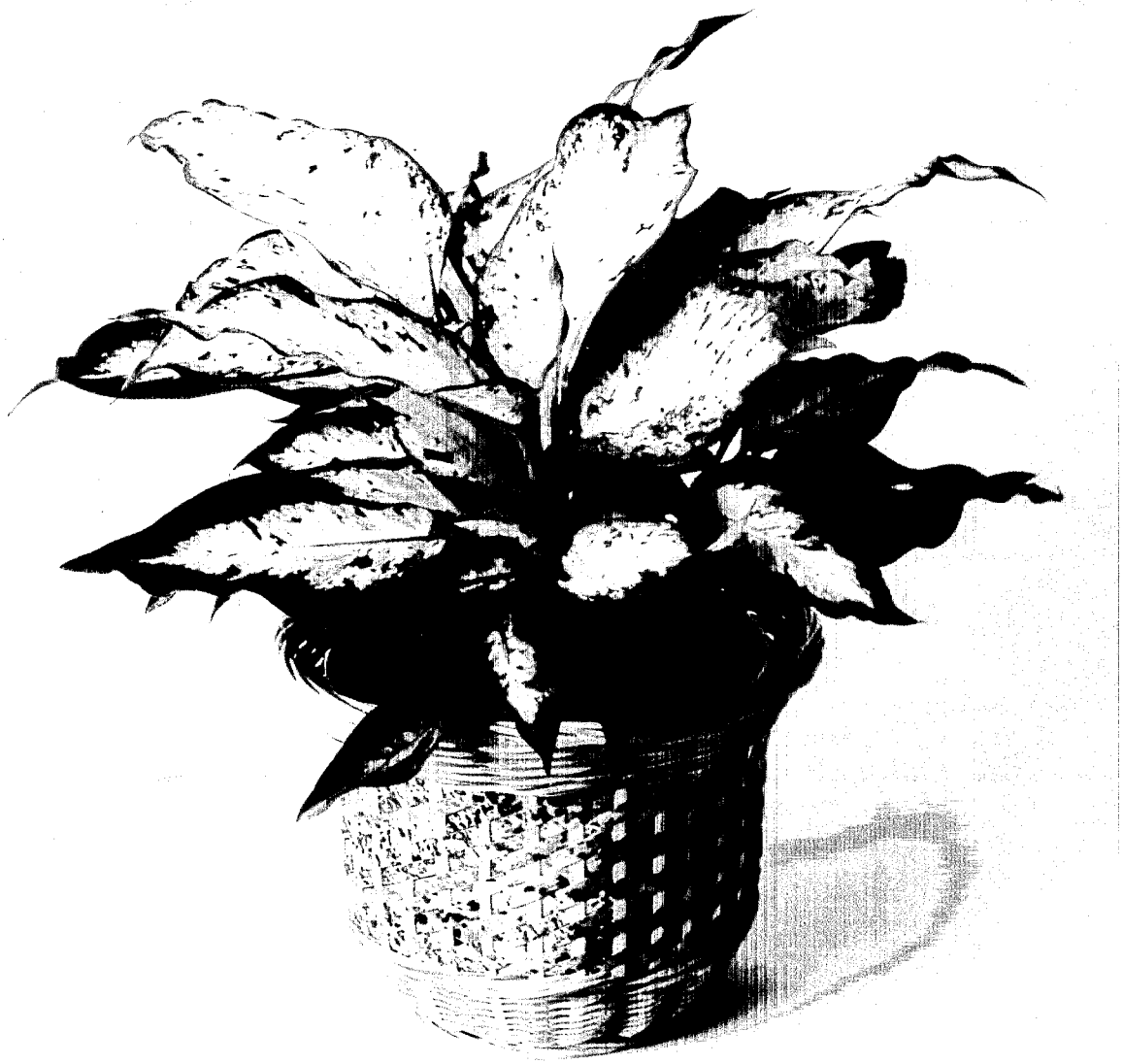

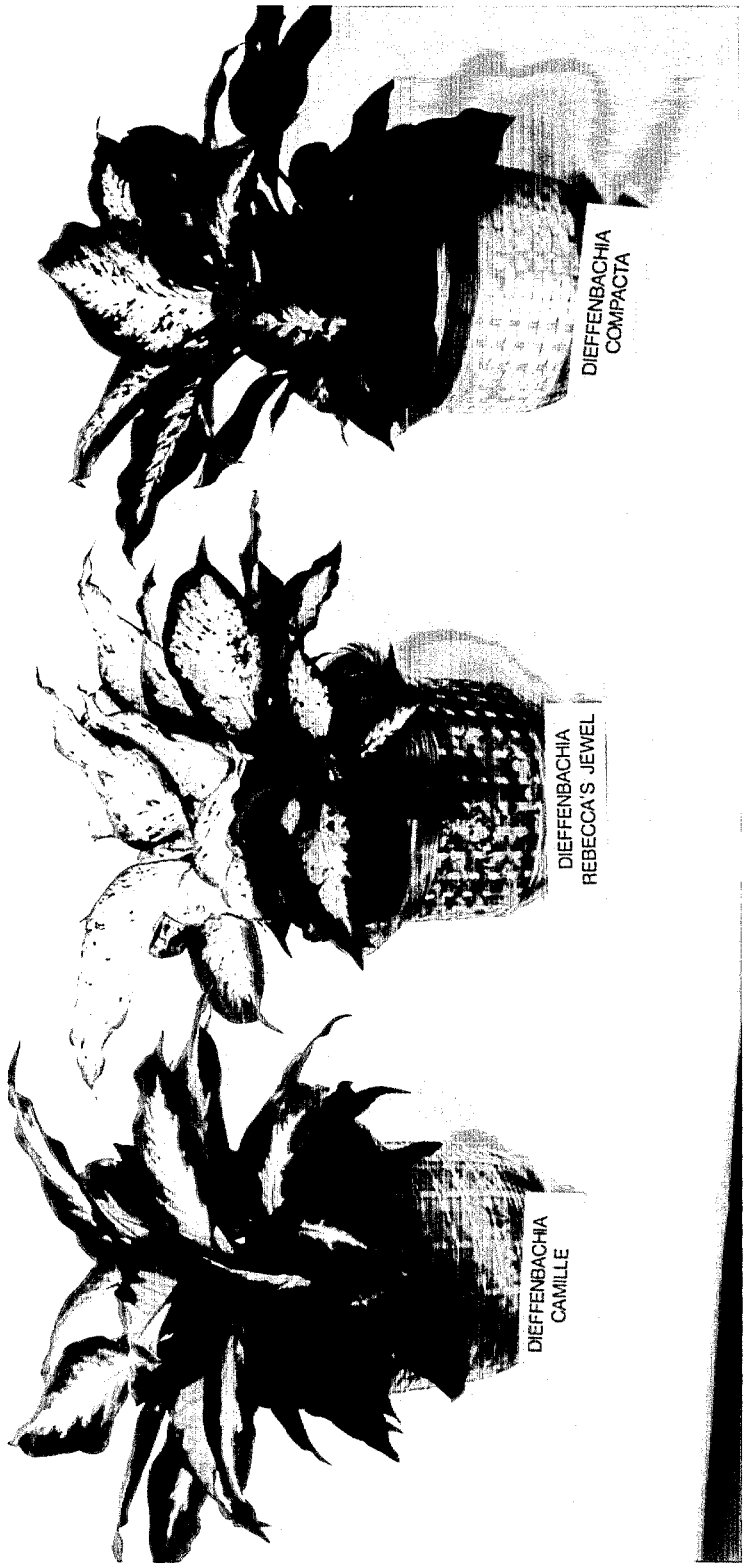
DIEFFENBACHIA
CAMILLE
DIEFFENBACHIA
REBECCA'S JEWEL
DIEFFENBACHIA
COMPACTA